US009711927B2

(12) United States Patent
Mourou et al.

(10) Patent No.: US 9,711,927 B2
(45) Date of Patent: Jul. 18, 2017

(54) HEURISTIC LASER DEVICE USING AN APPARATUS FOR PRODUCING LASER PULSES, AND CORRESPONDING HEURISTIC METHOD

(71) Applicant: Ecole Polytechnique, Palaiseau (FR)

(72) Inventors: Gerard Mourou, Paris (FR); Toshiki Tajima, Foothill Ranch, CA (US)

(73) Assignee: ECOLE POLYTECHNIQUE, Palaiseau (FR)

( * ) Notice: Subject to any disclaimer, the term of this patent is extended or adjusted under 35 U.S.C. 154(b) by 0 days.

(21) Appl. No.: 14/780,361

(22) PCT Filed: Mar. 27, 2014

(86) PCT No.: PCT/EP2014/056230
§ 371 (c)(1),
(2) Date: Sep. 25, 2015

(87) PCT Pub. No.: WO2014/154842
PCT Pub. Date: Oct. 2, 2014

(65) Prior Publication Data
US 2016/0043522 A1 Feb. 11, 2016

(30) Foreign Application Priority Data
Mar. 27, 2013 (FR) ..................... 13 52786

(51) Int. Cl.
*H01S 3/067* (2006.01)
*H01S 3/00* (2006.01)
(Continued)

(52) U.S. Cl.
CPC .......... *H01S 3/0057* (2013.01); *G01N 21/17* (2013.01); *H01J 27/24* (2013.01);
(Continued)

(58) Field of Classification Search
CPC ............... H01S 3/0057; H01S 3/06754; H01S 3/06758; H01S 3/10053; H01S 3/2383;
(Continued)

(56) References Cited

U.S. PATENT DOCUMENTS 9,130,344 B2 * 9/2015 Stadler ................ H01S 3/10007
2008/0084598 A1 4/2008 Rothenberg et al.
(Continued)

FOREIGN PATENT DOCUMENTS

EP 0980123 A2 2/2000
EP 1041686 A2 10/2000
(Continued)

OTHER PUBLICATIONS

International Search Report and Written Opinion dated May 15, 2014 for corresponding International Application No. PCT/EP2014/056230, filed Mar. 27, 2014.
(Continued)

*Primary Examiner* — Eric Bolda
(74) *Attorney, Agent, or Firm* — David D. Brush; Westman, Champlin & Koehler, P.A.

(57) ABSTRACT

A laser device includes an apparatus for producing amplified laser pulses, using a plurality of amplifying optical fibers, and groups the basic amplified pulses into an overall amplified pulse, as well as a target, onto which the overall amplified pulse is directed such as to generate a predetermined physical process thereon, which causes a change of state in the target. The laser device is configured to measure at least one distinctive parameter of the generated physical process; adjust at least one characteristic for adjusting the basic amplified laser pulses; and analyze a plurality of measurements for different adjustments. The device analyzes the measurements many times in loops for different laser pulse adjustment characteristics, enabling an optimi-
(Continued)

zation by a heuristic method. Also provided is a heuristic optimization method implemented by the laser device.

13 Claims, 4 Drawing Sheets

(51) Int. Cl.
| | |
|---|---|
| *H01S 3/10* | (2006.01) |
| *G01N 15/02* | (2006.01) |
| *G01N 21/17* | (2006.01) |
| *H01S 3/23* | (2006.01) |
| *H01J 27/24* | (2006.01) |

(52) U.S. Cl.
CPC ...... *H01S 3/06758* (2013.01); *H01S 3/10053* (2013.01); *H01S 3/2383* (2013.01)

(58) Field of Classification Search
CPC ............... G01N 21/17; G01N 21/1748; G01N 21/1761; G01N 21/1763
See application file for complete search history.

(56) References Cited

U.S. PATENT DOCUMENTS

| | | | | |
|---|---|---|---|---|
| 2009/0213879 A1* | 8/2009 | Stadler | ................ | H01S 3/10007 372/20 |
| 2010/0040095 A1* | 2/2010 | Mielke | ................ | H01S 3/0057 372/25 |
| 2012/0320450 A1* | 12/2012 | Starodoumov | ..... | H01S 3/10015 359/341.1 |
| 2013/0188244 A1 | 7/2013 | Kermene et al. | | |
| 2013/0336344 A1* | 12/2013 | Palese | ................ | H01S 3/1301 372/20 |
| 2014/0376001 A1* | 12/2014 | Swanson | ............. | A61B 5/0066 356/479 |

FOREIGN PATENT DOCUMENTS

| | | |
|---|---|---|
| EP | 1375052 A1 | 1/2004 |
| EP | 1927168 B1 | 12/2011 |
| EP | 2709429 A1 | 3/2014 |
| FR | 2964503 A1 | 3/2012 |
| JP | 2011216552 A | 10/2011 |
| WO | 2007034317 A2 | 3/2007 |

OTHER PUBLICATIONS

French Search Report and Written Opinion dated Dec. 18, 2013 for corresponding French Application No. FR1352786, filed Mar. 27, 2013.

International Preliminary Report on Patentability and English translation of the Written Opinion dated Sep. 29, 2015 for corresponding International Application No. PCT/EP2014/056230, filed Mar. 27, 2014.

* cited by examiner

HEURISTIC LASER DEVICE USING AN APPARATUS FOR PRODUCING LASER PULSES, AND CORRESPONDING HEURISTIC METHOD

1. CROSS-REFERENCE TO RELATED APPLICATIONS

This Application is a Section 371 National Stage Application of International Application No. PCT/EP2014/056230, filed Mar. 27, 2014, the content of which is incorporated herein by reference in its entirety, and published as WO 2014/154842 on Oct. 2, 2014, not in English.

2. FIELD OF THE INVENTION

An object of the present invention is a device comprising an apparatus for producing lasers pulses that strike a target to generate a physical process at this target.

It concerns in particular a device of this kind in which the apparatus can send out high-energy laser pulses at a high rate of repetition.

An object of the invention is also a method for optimizing characteristics of the laser pulse apparatus.

3. PRIOR-ART SOLUTIONS

Pulsed lasers are used in numerous devices known in the prior art. In these devices, the laser pulses can be directed onto a target in order to generate a predetermined physical process on this target.

For example, the physical processes that the laser can cause on the target can be a heating that can lead to a change in state of the target, for example for a welding laser, or it can lead to an optical pumping when the target is constituted by a doped amplifier medium. For certain applications, it is necessary for the laser to produce short high-energy laser pulses.

To obtain very short and very-high-energy laser pulses, a laser pulse produced by an oscillator is usually amplified in a laser amplifier capable of considerably increasing its power while at the same time preserving the phase coherence and the wavelength of the pulse.

There is in particular a fiber-optic amplifier, known from the document EP1927168, in which the initial laser pulse is distributed over a large number of amplifier optical fibers in which it is optically amplified. The amplified pulses in the different fibers are then gathered together to form an overall amplified pulse of very high energy.

For this overall pulse to be coherent, the phases of the amplified pulses in the different fibers need to be coordinated. The final overall pulse, which is a pulse formed by a plurality of light pulses juxtaposed with each other, thus has the characteristics of a coherent laser pulse.

Such a fiber amplifier can therefore produce very short laser pulses having very high energy. Besides, since such an amplifier can be efficiently cooled, it can also produce such pulses with a relatively high repetition rate, thus giving a series of pulses having a high average power. Finally, the energy efficiency of such a laser amplifier is very high. Such a series of pulses can be useful for several types of applications, for example for producing a relativistic proton beam as explained in the patent application EP12290303.2 filed on behalf of the present Applicant.

The characteristics of the laser pulses that strike the target affect the efficiency of the physical process generated by this pulse on the target. These characteristics, including the pulse duration, its amplitude, its wavelength, its spectral length and the shape of its wave front are therefore generally adapted so as to obtain high efficiency of the physical process generated on the target. The values enabling this high efficiency are often determined by computer simulations.

To be able to carry out such computer simulations, it is necessary to make a computer model of the target that is to be struck by the laser pulses. Generally, the target is given a configuration that makes it easy to model. The target can thus have a flat shape, or it can be constituted by a non-turbulent gas flow. Such configurations of targets, which are relatively easy to model, are often difficult to obtain, especially when the target is a plasma. In addition, they do not always constitute the configurations that give the highest efficiency of the physical process. Besides, when such a target is struck by a laser pulse, the pulse generates a disturbance in the target (especially a heating) which moves the characteristics away from the characteristics that have been modeled.

As a consequence, the simulations that are made on the basis of modeled targets are sometimes fairly distant from the real behavior of these targets. It is therefore difficult, through simulation, to determine the characteristics that the laser pulses must take in order to generate a physical process on the target with optimized efficiency.

Besides, when a laser amplifier successively amplifies a large number of pulses, at a high rate, the characteristics of the amplifier can evolve under the influence of the thermal effects of the amplification or under the influence of other uncontrolled disturbances. The characteristics of the laser pulses can thus evolve in time, and this makes the values of these characteristics move away from the values chosen to optimize the generation of the physical process.

4. SUMMARY OF THE INVENTION

An aspect of the present disclosure relates to a laser device comprising:
  an apparatus for producing amplified laser pulses using a plurality of amplifier optical fibers in which an initial laser pulse is distributed in order to be amplified therein, and means for gathering together elementary pulses amplified by the amplifier optical fibers into an overall amplified pulse, and
  a target on to which the overall amplified pulse is directed, to generate a predetermined physical process therein,
  and also comprising, according to the invention:
  means for measuring at least one characteristic parameter of the physical process generated by the overall amplified pulse,
  means for setting at least one characteristic for setting the amplified elementary laser pulses,
  means for analyzing a plurality of measurements delivered by the means for measuring, for different settings carried out by the setting means, determining an optimum setting of the setting characteristic or characteristics used to obtain an optimal value of the characteristic parameter or parameters of the physical process.

Thus, it is possible to optimize the generation of the physical process by the impact of an overall amplified pulse on a target more easily than in the prior art. Indeed, it is not sought here to obtain a laser having perfect characteristics to correspond to a target having a perfect configuration. On the contrary, it is sought, heuristically, i.e. by making successive trials to find the best solutions, to obtain the characteristics of setting that can be used to obtain an optimal value of the characteristic parameter or parameters of the physical process obtained by the interaction, with the real target, of the laser pulse on the target, leading to a change in its state. Thus, to optimize the laser pulse, it is not the characteristics of this pulse that are controlled but its efficiency, i.e. the result obtained with this pulse.

Since a fiber laser amplifier is used with this device, it is possible to modify a very large number of characteristics of the laser pulses very easily. Besides, such a fiber laser amplifier enables a high repetition rate that makes it possible, in a very limited time, to obtain a large number of measurements of the efficiency of the physical process arising out of the interaction of the laser pulse with the material of the target, for laser pulses having different characteristics.

According to one possible embodiment of the invention, the means for analyzing comprise means of random generation of values of at least one of the setting characteristics so as to generate a very large number of measurements taken into account by the analyzing means.

Advantageously, the means for setting comprise means for adjusting the phase of the amplified laser pulses in each of the amplifier fibers.

These means for adjusting the phase make it possible especially to modify the shape of the wave front of the amplified overall laser pulse.

Advantageously, the means for setting comprise means for adjusting the power of the laser pulses amplified in each of the amplifier fibers These means for adjusting the power make it possible to modify the power of the amplified overall laser pulse as well as its spatial distribution of amplitude or of power.

According to a preferred embodiment, the physical process generated by the interaction of the laser pulse on the target is an emission of a particle beam, for example an emission of a proton beam.

The device can thus activate nuclear reactions such as the transmutation of radioactive wastes.

Advantageously, the means for setting enable the modifying of at least one of the following characteristics of the overall laser pulse:
  shape of the wave front of the pulse;
  power of the pulse;
  spatial distribution of amplitude of the pulse;
  spectral amplitude or spread of the pulse;
  spatial or temporal spread of the spectral components of the pulse;
  spatial or temporal distribution of amplitude of the pulse;
  duration of the pulse.

Many characteristics of the pulse can be adapted so that the pulse shows characteristics that optimize the physical process arising out of the interaction between the laser pulse and the target. It must be noted that these different parameters are often arbitrarily fixed in prior art solutions.

Advantageously, the apparatus for producing laser pulses enables the production of laser pulses at a frequency higher than 1 kHz and preferably higher than 10 kHz.

Such a rate of repetition, which is possible with fiber laser amplifiers, enables the efficient choice, within a reasonable period of time, of the pulse characteristics that will optimize the physical process causing a change in state of the target.

Advantageously, the means for setting modify the characteristics of the overall laser pulses produced at a frequency higher than 100 Hz and preferably higher than 1 kHz.

Such a frequency of modification of the characteristics of the laser pulses implements the method of the invention efficiently.

The invention also relates to a method for optimizing a predetermined physical process generated on a target by a laser pulse, said method comprising the following steps:
  a step for producing an amplified laser pulse comprising:
    a sub-step for setting the characteristics of operation of each amplifier optic fiber of a fiber laser amplifier,
    a sub-step for distributing an initial laser pulse in the amplifier optical fibers, and
    a sub-step for grouping amplified pulses in the amplifier optical fibers into an overall amplified laser pulse;
  a step of impact of the overall amplified laser pulse on a target that can generate a predetermined physical process therein;
  a step for measuring the efficiency of the physical process according to at least one predetermined criterion;
  the steps for producing an impact and measurement pulse being repeated in a loop several times.

According to the invention, this method comprises a step for determining characteristics of operation of the plurality of amplifier optical fibers used to obtain optimal efficiency of the physical process arising out of the interaction of the laser pulse with the material of the target. The determining is done through the analysis of results obtained earlier during the steps for measuring carried out for the different settings.

It is therefore from a series of trials under real conditions of operation that the characteristics of operation of the amplifier optical fibers to be used are determined and not from computations, simulations or hypotheses.

Advantageously, the sub-step for setting characteristics of operation of each amplifier optical fiber comprises a setting of the pulse phase passing through each amplifier optical fiber.

Advantageously, the sub-step for setting the characteristics of operation of each amplifier optical fiber comprises a setting of the power of the amplified pulse in each amplifier optical fiber.

5. LIST OF FIGURES

The invention will be understood more clearly from the following description of preferred embodiments given by way of a non-exhaustive illustration and from the appended drawings, of which:

6. DESCRIPTION OF ONE EMBODIMENT 6.1 Fiber Laser Amplifier

Figure 1:
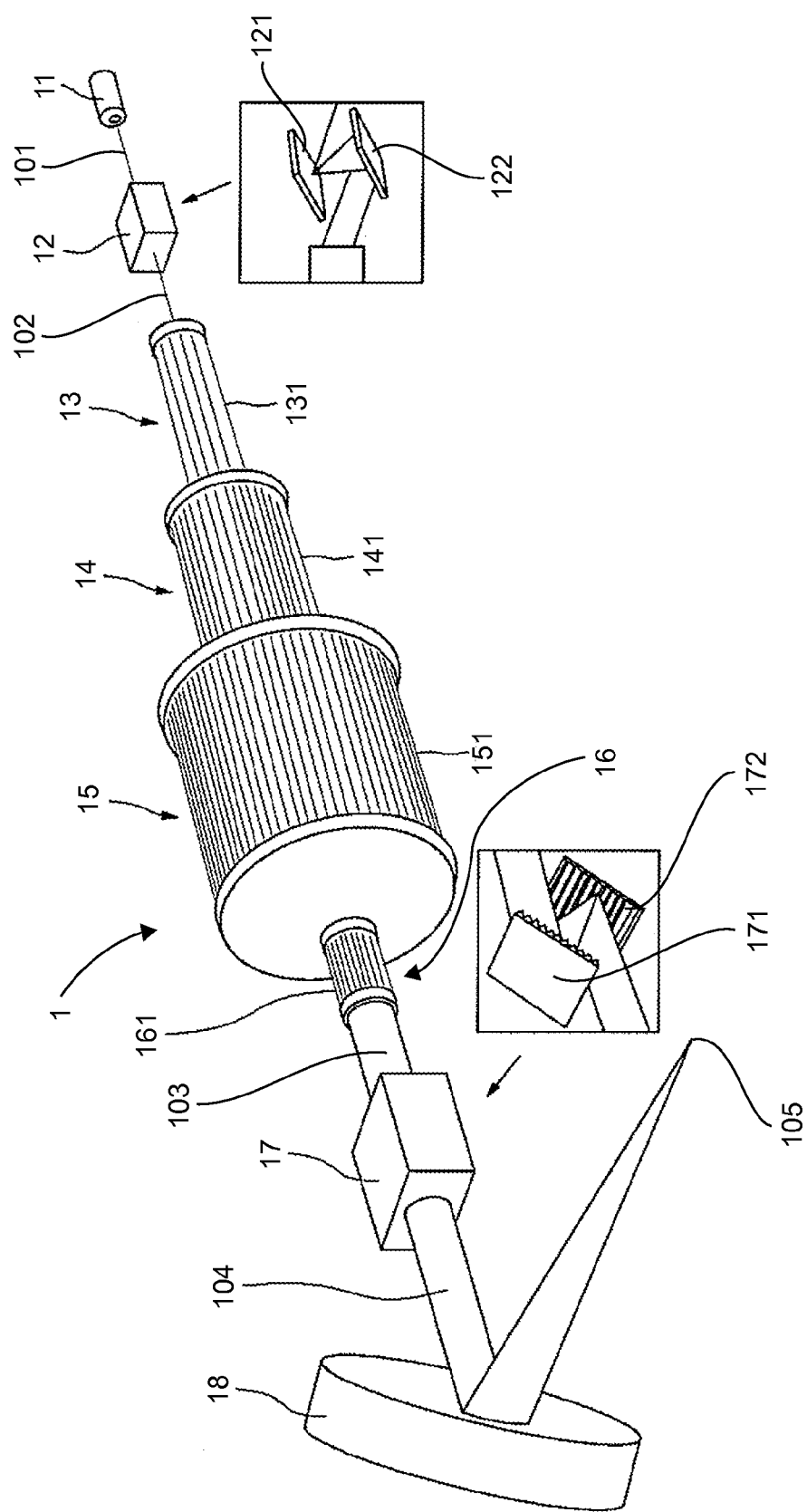
FIG. 1 is a schematic representation of an apparatus for producing high-energy laser pulses.

FIG. 1 represents the apparatus 1 for producing high-energy laser pulses.

In this apparatus 1, a low-energy laser pulse 101 is produced by an oscillator 11. In the embodiment shown, this pulse 101 is then temporally stretched by a stretcher 12 comprising a pair of diffraction gratings 121 and 122 having the effect of temporally offsetting the different spectral components of the original low-energy pulse 101. The stretched pulse 102 then has a peak power that is lower and a duration that is lengthier than that of the pulse 101.

This laser pulse 102 is then distributed amongst a plurality of amplifier fibers 131 forming a first amplification stage 13 of the fiber laser amplifier. The different fibers are separated from one another so that they can efficiently carry out their cooling. Each of the amplifier fibers 131 has a core made of doped material and is optically pumped so as to optically amplify the laser pulse circulating in the fiber. The pulse passing through each of the amplifier fibers 131 is then amplified. Then it is itself distributed amongst a plurality of amplifier fibers 141 forming the second stage of amplifications 14 of the fiber laser amplifier. Again, the pulse passing through each of these amplifier fibers 141 is amplified, and is then itself distributed amongst a plurality of amplifier fibers 151 forming the third stage of amplifications 15 of the fiber laser amplifier. Thus, in each amplification stage, the pulse is amplified in a plurality of fibers independent of each other and then divided so that the lower-power pulses are transmitted to each of the higher-level amplification fibers.

The third and last amplification stage 15 then comprises a very large number of amplifier fibers, for example of the order of $10^6$. Each of the amplifier fibers of this third stage is extended by a transmission fiber 161 having a very low loss rate. The transmission fibers are assembled into a bundle 16 so that the pulses coming out of each of the ends of these transmission fibers 161 are sent in parallel and in juxtaposition. These pulses then form a single amplified overall pulse 103.

In the embodiment shown, this amplified overall pulse is compressed temporally by a compressor 17 comprising a pair of diffraction gratings 171 and 172 temporally grouping the different spectral components of the pulse. The pulse 104 coming out of this temporal compressor 17 then has very high energy and a very short duration. It can for example, as shown in FIG. 1, be focused on a point 105 by means of a concave mirror 108.

6.2 Adjusting the Characteristics of the Laser Pulse

Amplifying the original pulse 101 in a plurality of amplifier fibers enables a precise adjusting of several of the characteristics of the final amplified laser pulse 104.

Figure 2:
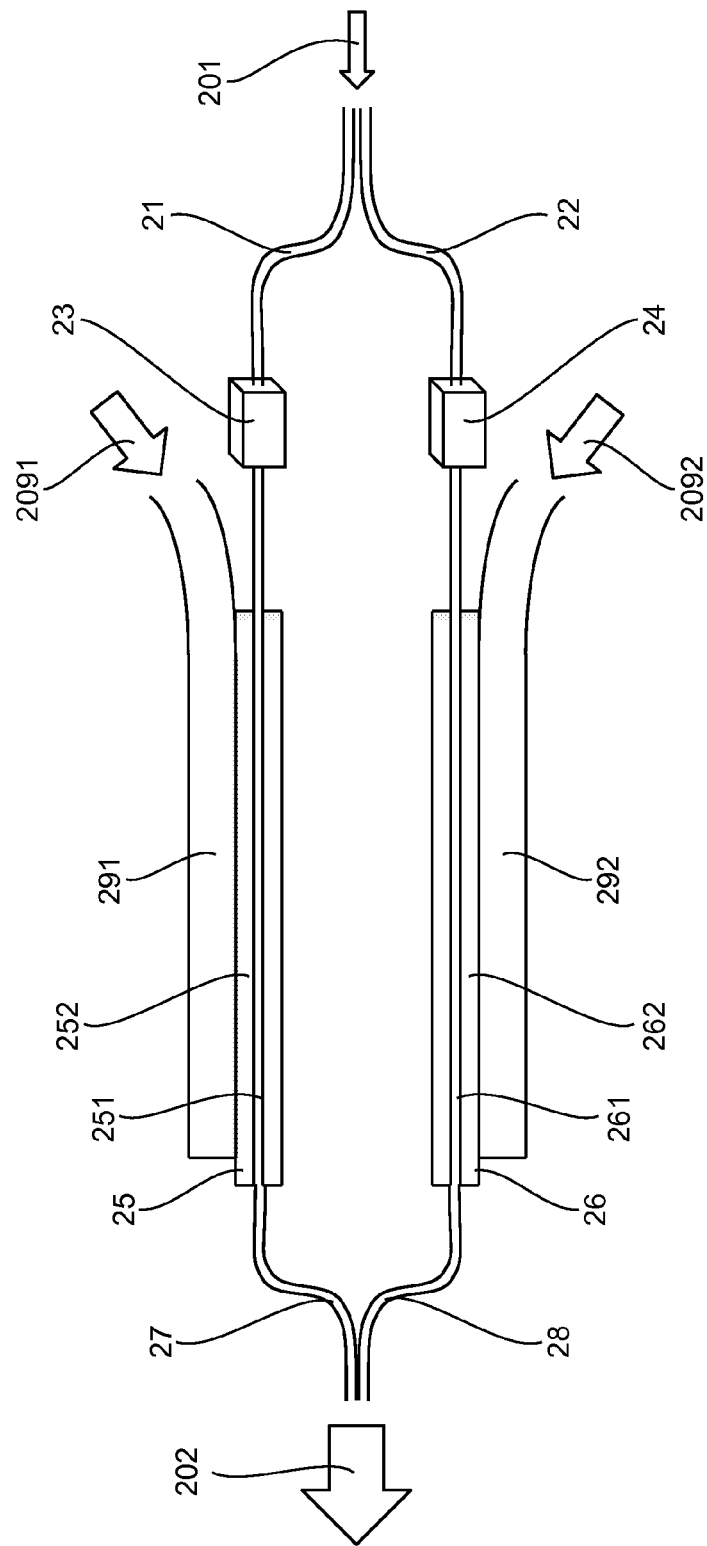
FIG. 2 is a schematic representation of two of the amplifier fibers of the apparatus for producing laser pulses of FIG. 1.

FIG. 2 schematically illustrates two of the amplifier fibers taken from amongst the amplifier fibers of the apparatus for producing laser pulses 1 of FIG. 1. This figure is of course not drawn to scale since the fibers actually are of great length. A laser pulse 201 to be amplified coming for example from an amplifier fiber of a lower amplification stage is sent simultaneously in two optical fibers 21 and 22.

The optical fiber 21 leads this pulse up to an amplifier fiber 25 in passing through a modulator 23. The modulator 23 is a crystal, the length of which can be adjusted according to need. It can for example be an electro-optical modulator constituted by a piezoelectric crystal, the length of which varies as a function of a voltage applied to its terminals. According to another possible embodiment, it can be an acousto-optic crystal, the length of which varies as a function of a mechanical wave applied to it. Such a modulator 23 enables the variation, as needed, of the length of the path crossed by the light pulse.

The amplifier fiber 25 has two cores. Its central core 251 is made of a doped laser material and leads the light pulse coming from the optical fiber 21. A peripheral core 252 surrounding the central core 251 leads the pumping light intended to optically pump the laser material of the central core 251. This pumping light can be transmitted in this peripheral core by a supply fiber 291 into which the light of a pumping laser diode 2091 is sent. Thus, the laser material of the central core 251 is pumped optically and the laser pulse flowing in its core is amplified optically.

Since the central core of the fiber has mono-mode type propagation characteristics, each amplifier fiber behaves like a perfect amplifier. At the exit from the amplifier fiber 25, the laser pulse coming from the central core 25 is conducted by a transmission fiber 27.

In the same way, the optical fiber 22 conducts the pulse 201 up to an amplifier fiber 26 in passing through a modulator 24. This pulse travels through the central core 261, made of doped laser material, of the amplifier fiber 26, which has preliminarily been optically pumped by the light of a laser pumping diode 2092 having passed through a supply fiber 292 and then through the peripheral core 262 surrounding the central core 261. The laser pulse flowing in this central core 261 is therefore optically amplified and then exits into a transmission fiber 28.

At the end of the bundle formed by the different transmission fibers, including the fibers 27 and 28, an overall amplified pulse 202 is formed. This pulse is advantageously formed by a large number of elementary pulses, for example of the order of $10^6$, each derived from an amplifier fiber. After a certain length of propagation, this overall amplified pulse, which is composite because it comes from elementary pulses coming from each of the fibers, has the characteristics of a unique pulse. However, the composite nature of this pulse makes it possible to vary certain characteristics easily.

Power Variation

Thus, since the power of laser pulse emitted by each amplifier fiber can vary according to the power of the pumping laser diode pumping this fiber, it is possible at will to obtain variation in the power of each elementary pulse forming the overall amplified pulse. The variation of the pumping power and hence the variation of the power of the amplified elementary pulse can be obtained very easily, with high precision of the order of 1%, and with a response time of the order of 1 millisecond (kHz). Thus, in making the power of each of the amplified elementary pulses vary in a coordinated fashion, it is possible to make the spatial distribution of amplitude or spatial distribution of power of the overall amplified pulse vary as desired.

Thus, depending on need, it is possible to obtain a Gaussian or hyper-Gaussian spatial distribution of amplitude or, on the contrary, a uniform distribution or any other type of distribution. It is also possible clearly to obtain a variation in the same way of the total power of the overall amplified pulse.

Variation of the Wave Front

Moreover, the modulators, especially 23 and 24, that are present on the path of each elementary pulse make it possible to vary the length of the path of the pulses. It is thus possible to set the phase of each elementary pulse and therefore give the wave front of the overall amplified pulse 202 the desired shape with high precision. Since the modulators have a very fast response time, it is possible to change the shape of the wave front with a high frequency, of the order of 1 kHz.

Other parameters are used to influence the phase of an elementary pulse amplified by an amplifier fiber. Thus, when the power of a pumping laser is made to vary, the release of heat at the amplifier fiber is made to vary. This variation of heat can give rise to an expansion or a shrinkage of this fiber in its entirety, which then modifies the phase of the pulse at the exit from the transmission fiber.

It can be that such a phase variation is not desired if it is sought only to modify the rate of amplification in the fiber and therefore the power of the output pulse without changing its phase. In this case, it is possible to compensate for an expansion or a shrinkage by acting simultaneously on the corresponding modulator in order to preserve an identical phase at output. In other cases, on the contrary, it is desirable to make the power of the pulse and its phase vary simultaneously.

In one specific embodiment, it is possible that the amplifier fiber will be doped by two types of distinct doping particles. A first type of doping particle classically makes it possible to produce the laser reaction amplifying the pulse. The second type of doping particles, chosen so as not to interfere with the wavelength of the pulse to be amplified, has the sole purpose of generating thermal effects in the fiber. A specific pumping laser can be provided to pump these doping particles of the second type and thus generate thermal effects that make the phase of the laser pulse vary without causing its power to vary.

Variation of the Other Characteristics of the Pulse

It is also possible to act on other characteristics of the overall amplified pulse. For example, a variation can be obtained in the spectral distribution of the pulse. To this end, the pulse needs to be spectrally decomposed so that the different spectral components are amplified by different amplifier fibers. Each spectral component can then be amplified distinctly. If the fibers conveying the different spectral components are distributed uniformly in the bundle of fibers that are used to send the overall amplified pulse, it is also possible to obtain variation in the spectral distribution of the spectral components in this pulse.

Depending on the use of the amplified pulses, those skilled in the art can thus think of a large number of parameters which can be influenced in order to optimize the pulse.

6.3 Use of Laser Pulses to Produce a Physical Process

Figure 3:
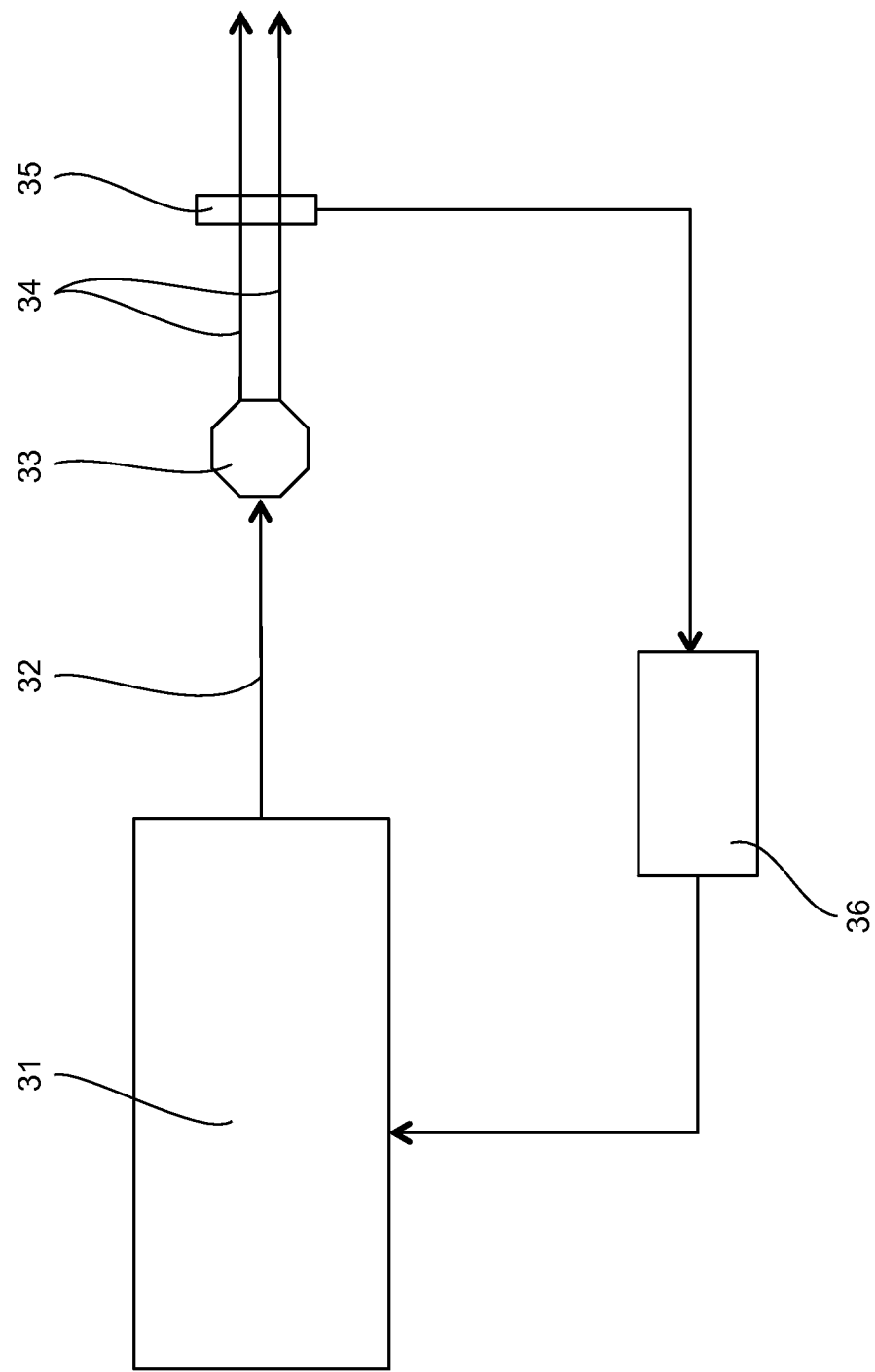
FIG. 3 is schematic representation of a system according to one embodiment of the invention implementing an apparatus for producing laser pulses to generate a physical process when the laser pulses strike the target, leading to a change in state of this target.

FIG. 3 is a schematic representation of a laser device according to one embodiment of the invention implementing an apparatus for producing laser pulses 31 to generate a physical process arising out of the interaction of the laser pulse with the target. This apparatus for producing laser pulses comprises a fiber laser amplifier, for example of the type represented by FIG. 1.

This apparatus produces an amplified laser pulse, represented by the arrow 32, that is directed to a target 33. For example, in the embodiment represented, this target 33 can be a hydrogen (H) film or helium (He) film. According to the invention, it is not necessary for this target to take a particular form aimed at facilitating its modeling. Indeed, it is not necessary, according to the invention, to use simulations to determine the characteristics that the laser pulses must take.

After impact on the target 33, the laser pulse 32 produces a physical process. For example if the laser pulse has sufficient energy then, when it strikes the target, it generates a relativistic proton beam 34 starting from the target 33 at the speed of light. This proton beam 34 can thereafter be used to generate other reactions.

Measurement of the Physical Process

Means 35 of measurement make it possible to measure the efficiency of the physical process occurring at the target 33 when it is struck by the laser pulse. In the example shown, these means of measurement are formed by two sensors, one used to count the number of protons 34 sent out by the target 33 when its material interacts with the laser pulse and the other used to measure the energy of these protons.

6.4 Heuristic Method for Setting Laser Pulses

The measurements of the efficiency of the physical process arising out of the interaction of the laser pulse with the target and prompting a change in state of this target, that are taken by the sensor 35, are sent to computation means, for example constituted by a computer 36. This computer 36 can also control the different parameters by which the characteristics of the laser pulse 32 are made to vary. It can for example control the modulators and the pumping laser diodes for each of the amplifier fibers of the apparatus 31 for producing laser pulses. Thus, this computer can obtain variation in the characteristics of the laser pulse 32 between two pulses.

Thus, when it is desired to use the laser pulse to produce a physical process, it is possible to fire a first laser pulse 32 with arbitrarily chosen characteristics. During this first firing operation, the computer 36 records the measurements of efficiency of the physical process and then modifies the characteristics of the laser pulse 32 before a second firing operation. Numerous successive firings of laser pulses 32 can thus be achieved with different characteristics, especially in terms of wave-front shape and spatial distribution of amplitude. The efficiency of the physical process is measured for each firing in order to determine the characteristics of the laser pulse that enable the best efficiency to be obtained.

This series of laser pulse firings intended to enable the computer to determine the best-suited characteristics of the laser pulse can be done in a restricted period of time. Indeed, while the apparatus 31 for producing laser pulses is of the type shown in FIG. 1, it can carry out laser pulse firings at very high frequency ranging up to 10 kHz. The variations in characteristics of the laser pulse 32 produced, and especially of the power, of the spatial distribution of amplitude and of the shape of the wave front can be done at frequency of the order of 1 kHz.

The computer can therefore carry out a large number of measurements in a restricted time on predetermined ranges of values for each parameter, or values that are determined by the computer itself according to the measured results of the efficiency of the physical process. Once these measurements are made, then, depending on the program that it executes, the computer can choose to continue to carry out a laser pulse firing 32 with the tested parameters enabling the best efficiency of the physical process according to a predetermined criterion or it can carry out a new series of firing operations on restricted ranges of values for the different parameters, these restricted ranges of values appearing to be promising in the light of the results of the first series of firings.

It must be noted that the computer 36 does not set up an automatic feedback control of the apparatus 31 for producing laser pulses linked to the results measured by the sensor 35. Indeed, to achieve such an automatic control, it would be necessary to know those parameters of the apparatus 31 for producing laser pulses that must be acted upon to obtain a desired modification of the output measurement. Here, on the contrary, the excessively large number of parameters that can be acted upon prevents the use of a classic feedback control loop.

On the contrary, the system comprising the apparatus 31 for producing laser pulses, the target 33, the sensor 35 and the computer 36 is heuristic in that it carries out a series of trials that may be more conclusive or less conclusive and in that, depending on the results of these trials, it determines the conditions in which it can work in the most efficient way. The system therefore makes successive approaches in gradually eliminating the alternatives and in preserving only one restricted range of solutions tending towards the optimal solution.

Once the computer 36 has determined the optimum combination of parameters for the laser pulses 32, the system can continue to work according to these parameters. In certain cases, it can be however useful, during operation, to again test the different parameters in order to ascertain that the optimal conditions of operation have not changed. It must be noted that these parameters, which especially take account of the real shape of the target 33, can be determined by means of this heuristic type operation without the shape of the target being known.

6.5 Heuristic Method for Optimizing the Physical Process

Figure 4:
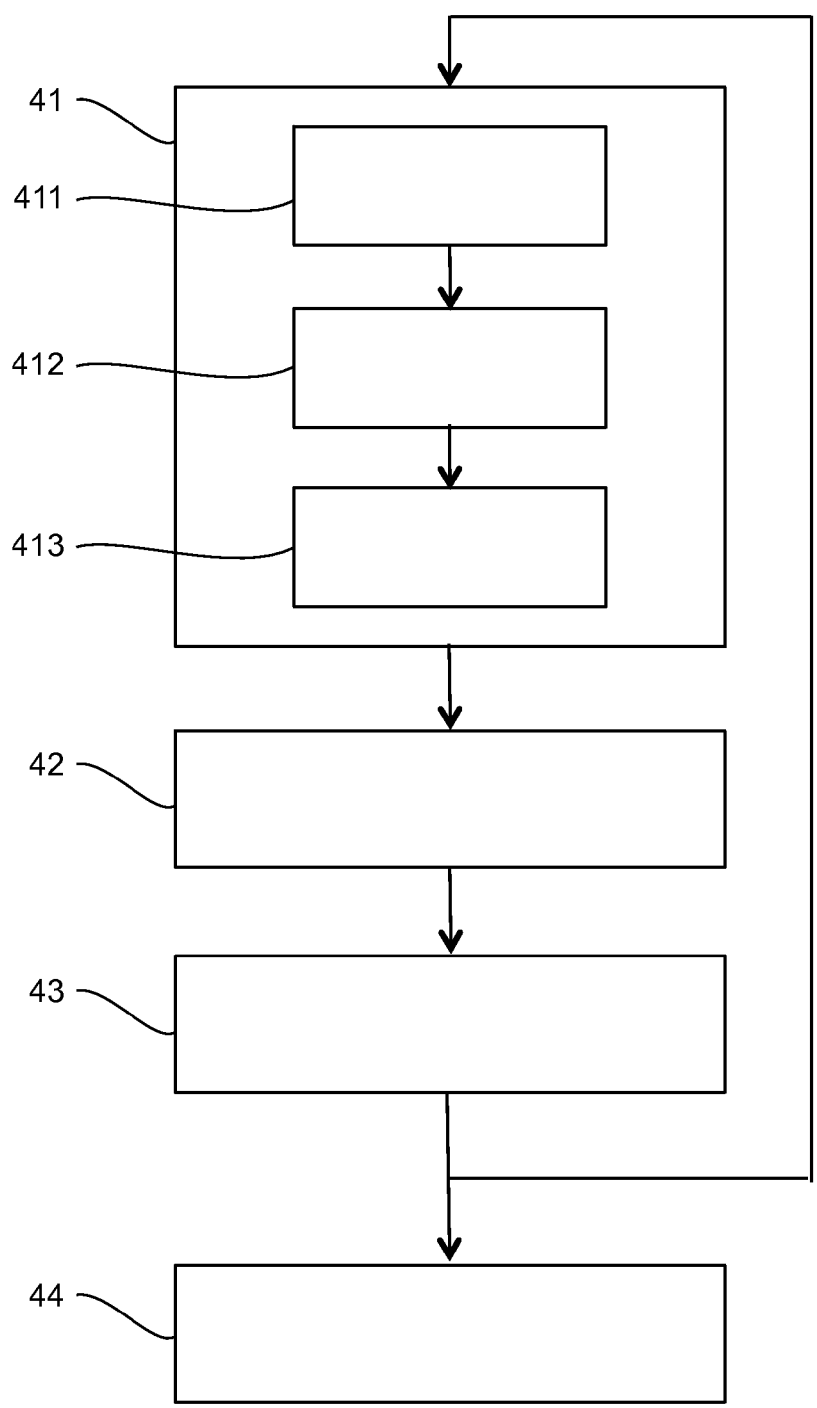
FIG. 4 is a schematic representation of the steps of a method of heuristic optimization according to the invention.

FIG. 4 is a schematic representation of the steps of the heuristic method for optimizing a physical process generated on a target by a laser pulse according to the invention.

The general principle of this method is that, in the same way as the laser device according to the present invention, it comprises the following steps:
- a step (41) for producing an amplified laser pulse, amplified at a frequency higher than 100 Hz by a plurality of amplifier optical fibers in which an initial laser pulse (101) is distributed to be amplified therein, said elementary pulses amplified by said amplifier optical fibers being gathered together into an overall amplified pulse, a step (42) of impact of said overall amplified pulse on a target for the generation therein of a predetermined physical process leading to a change in state of said target;

and particularly according to the invention:
- a step (43) for measuring at least one characteristic parameter of said physical process generated during the impact of said overall amplified pulse on said target;
- a step (411) for setting at least one characteristic of the setting of said amplified elementary laser pulses, said at least one characteristic being predetermined as the function of the use of said amplified elementary laser pulses;

the steps for producing a pulse, making an impact, measuring and setting being repeated at least twice delivering a plurality of measurements for different settings, and in addition, according to the invention:
- a step (44) for determining an optimal setting of said characteristic or characteristics of setting to obtain an optimal value of said characteristic parameter or parameters of the physical process on the basis of said plurality of measurements delivered for different settings.

More specifically, this method comprises a step 41 for producing an amplified laser pulse that is carried in an apparatus for producing laser pulses comprising a fiber laser amplifier. This step 41 itself comprises:
- a sub-step 411 for setting characteristics of operation of each amplifier optical fiber of the fiber laser amplifier, for example the length of the optical path, to modify the phase of the pulse passing through the fiber or to modify the pumping power to modify the rate of amplification of the pulse passing through the fiber;
- a sub-step 412 for distributing an initial laser pulse in the amplifier optical fibers; and
- a sub-step 413 for gathering together the amplified fibers in said amplifier optical fibers into an overall amplified laser pulse.

The method then comprises a step 42 of impact of the overall amplified laser pulse on a target for the generation therein of a physical process corresponding to a change of at least one part of the target when the laser pulse interacts with the material of the target and a step 43 for measuring the efficiency of this physical process.

These three steps for producing, a pulse 41, an impact 42, and for measuring 43 are repeated in a loop many times. It is thus possible to measure the efficiency, in other words at least one characteristic parameter, of the physical process for a large number of configurations (settings) of the characteristics of operation of each amplifier optical fiber of the fiber laser amplifier.

After these steps are repeated several times, a step 44 can be implemented for choosing characteristics of operation of said plurality of amplifier optical fibers used to obtain an optimal efficiency of the physical process according to a predetermined criterion. This criterion can for example be the power of the physical process generated by the impact of the laser pulse on at least one part of the target.

It must be noted that the step 44 for choosing characteristics of operation can be done on a microprocessor. This same microprocessor can also advantageously command the sub-steps 411 for setting characteristics of operation of each amplifier optical fiber of the fiber laser amplifier before the sub-steps 412 are carried out.

6.6 Conditions of Application

A heuristic system according to the invention can be used for numerous applications. However, a heuristic type of operation can be implemented efficiently only when the firing frequency or repetition rate of the apparatus for producing laser pulses is great, i.e. greater than 100 Hz and preferably greater than 1 kHz. If not, there is a risk that the large number of trials necessitated by the heuristic type approach will take an excessively large amount of time.

Besides, such a heuristic system has particular value when the laser amplifier used is a fiber amplifier, for example of the type shown in FIG. 1. Indeed, in such a laser amplifier in which the overall amplified pulse is formed by a plurality of elementary pulses that are amplified in independent amplifier fibers, the number of parameters that can influence the overall amplified pulse is extremely great. The heuristic type operation makes it possible, in such a laser, to finely optimize the parameters that were not optimized in the prior art, such as the shape of the wave front and the spatial distribution of amplitude of the pulse.

6.7 Other Possibilities of Application

In the embodiment presented here above, the firing of the laser pulses on the target generates a relativistic proton beam. A system according to the invention can however be implemented for other applications in which laser pulses are emitted on a target in order to generate physical processes therein. In this case, the heuristic type operation can be done by analyzing the characteristics of the physical process generated on the target.

Those skilled in the art could thus imagine numerous other possible applications of a system or a method according to the invention.

An exemplary embodiment of the present application provides a device using a pulsed laser, the characteristics of which are optimized to generate a physical process on a target struck by the laser pulses, with optimized efficiency.

An embodiment provides a device of this kind in which a great number of characteristics of the pulsed laser are optimized to optimize the physical process on the target.

An embodiment provides a device of this kind in which the target can have various configurations that are difficult to model, without impairing the efficiency of the physical process generated by the pulsed laser.

An embodiment provides a device of this kind that optimizes the generation of a physical process on the target when uncontrolled disturbances affect the characteristics of the laser pulses produced.

Although the present disclosure has been described with reference to one or more examples, workers skilled in the art will recognize that changes may be made in form and detail without departing from the scope of the disclosure and/or the appended claims.

The invention claimed is:

1. A laser device comprising:
an apparatus configured to produce amplified laser pulses at a frequency higher than 100 Hz, using a plurality of amplifier optical fibers in which an initial laser pulse is distributed in order to be amplified therein, and to gather together elementary pulses amplified by said amplifier optical fibers into an overall amplified pulse, and
a target on to which said overall amplified pulse is directed, to generate therein, after impact, a predetermined physical process leading to a change in state of said target,
means for measuring at least one characteristic parameter of said physical process generated after impact by said overall amplified pulse on said target,
means for setting at least one setting characteristic of said amplified elementary laser pulses, said at least one characteristic being predetermined as a function of the use of said amplified elementary laser pulses;
means for analyzing a plurality of measurements delivered by said means for measuring, for different settings made by said means for setting, during which said apparatus, said means for measuring and said means for setting are implemented at least twice, determining an optimal setting of said setting characteristic or characteristics to obtain an optimal value of said characteristic parameter or parameters of the physical process.

2. The laser device according to claim 1, wherein said means for setting comprise means for adjusting a phase of the amplified laser pulses in each of the amplifier fibers.

3. The laser device according to claim 1, wherein said means for setting comprise means for adjusting power of the laser pulses amplified in each of the amplifier fibers.

4. The laser device according to claim 1, wherein the physical process generated by the interaction of the laser pulse on the target is an emission of a particle beam.

5. The laser device according to claim 4, wherein the physical process generated by interaction of said laser pulse on the target is an emission of a proton beam.

6. The laser device according to claim 1, wherein said means for setting enable modifying at least one of the following characteristics of the overall laser pulse:
shape of the wave front of the pulse;
power of the pulse;
spatial distribution of amplitude of the pulse;
spectral amplitude or spread of the pulse;
spatial or temporal spread of the spectral components of the pulse;
spatial or temporal distribution of amplitude of the pulse;
duration of the pulse.

7. The laser device according to claim 1, wherein said apparatus enables production of laser pulses at a frequency higher than 1 kHz.

8. The laser device according to claim 1, wherein said means for setting modify the characteristics of the overall laser pulses produced at a frequency higher than 100 Hz.

9. A method for optimizing a predetermined physical process generated on a target by a laser pulse, said method comprising:
producing an amplified laser pulse, amplified at a frequency higher than 100 Hz by a plurality of amplifier optical fibers over which an initial laser pulse is distributed in order to be amplified therein, said elementary pulses amplified by said amplifier optical fibers being gathered together into an overall amplified pulse,
impacting said overall amplified pulse on a target to generate therein a predetermined physical process leading to a change in state of said target;
measuring at least one characteristic parameter of said physical process generated during the impact of said overall amplified pulse on said target,
setting at least one setting characteristic of said amplified elementary laser pulses, said at least one characteristic being predetermined as a function of the use of said amplified elementary laser pulses;
repeating said producing a pulse, impacting, measuring and setting at least twice delivering a plurality of measurements for different settings,
determining an optimal setting characteristic or characteristics to obtain an optimal value of said characteristic parameter or parameters of the physical process from said plurality of measurements delivered for different settings.

10. The method according to claim 9, wherein setting at least one setting characteristics of said amplified elementary laser pulses comprises setting a phase of the pulse passing through each amplifier optical fiber.

11. The method according to claim 9, wherein setting at least one setting characteristics of said amplified elementary laser pulses comprises setting a power of the amplified pulse in each amplifier optical fiber.

12. The laser device according to claim 1, wherein said means for setting enable modifying duration the overall laser pulse.

13. The method according to claim 9, wherein said setting modifies a duration the overall laser pulse.

* * * * *